United States Patent
Schuele et al.

(10) Patent No.: US 11,833,031 B2
(45) Date of Patent: Dec. 5, 2023

(54) OPTIMIZED WRITING OF REFRACTIVE INDEX STRUCTURES IN IOLS USING VARIABLE PASSES

(71) Applicant: AMO Development, LLC, Irvine, CA (US)

(72) Inventors: Georg Schuele, Portola Valley, CA (US); David A. Dewey, Sunnyvale, CA (US); Jenny Wang, Mountain View, CA (US); Richard Hofer, Santa Cruz, CA (US); Alexander Vankov, Mountain View, CA (US)

(73) Assignee: AMO Development, LLC, Irvine, CA (US)

( * ) Notice: Subject to any disclaimer, the term of this patent is extended or adjusted under 35 U.S.C. 154(b) by 227 days.

(21) Appl. No.: 17/057,687

(22) PCT Filed: Apr. 9, 2020

(86) PCT No.: PCT/IB2020/053419
§ 371 (c)(1),
(2) Date: Nov. 22, 2020

(87) PCT Pub. No.: WO2020/208583
PCT Pub. Date: Oct. 15, 2020

(65) Prior Publication Data
US 2022/0061983 A1    Mar. 3, 2022

Related U.S. Application Data

(60) Provisional application No. 62/944,328, filed on Dec. 5, 2019, provisional application No. 62/832,825, filed on Apr. 11, 2019.

(51) Int. Cl.
*A61F 2/16* (2006.01)
*A61F 9/008* (2006.01)
*B29D 11/02* (2006.01)

(52) U.S. Cl.
CPC ............ *A61F 2/1656* (2013.01); *A61F 9/008* (2013.01); *B29D 11/023* (2013.01); *A61F 2009/00897* (2013.01); *A61F 2240/001* (2013.01)

(58) Field of Classification Search
CPC ................... A61F 2/1656; A61F 9/008; A61F 2009/00897; A61F 2240/001;
(Continued)

(56) References Cited

U.S. PATENT DOCUMENTS 7,969,654 B1    6/2011 Ersoy et al.
8,932,352 B2    1/2015 Knox et al.
(Continued)

OTHER PUBLICATIONS

Aristizabal S.L., et al.,"Microlens Array Fabricated by a Low-Cost Grayscale Lithography Maskless System," Optical Engineering, 2013, vol. 52 (12), pp. 125101, (https://doi.org/10.1117/1.OE.52.12.125101).

(Continued)

*Primary Examiner* — Scott M. Getzow
(74) *Attorney, Agent, or Firm* — Johnson & Johnson Surgical Vision, Inc.

(57) ABSTRACT

A laser scanning method for forming a Fresnel type gradient index lens in an intraocular lens IOL. The radial profile of the desired optical pathlength (OPL) difference to be achieved in the IOL has multiple zones, each zone ramping from unchanged OPL to one wave, and stepping down to zero. To form a zone of a predefined OPL difference profile, the laser beam is scanned in multiple passes; in each pass, the laser beam is scanned in concentric circles of varying radii covering all or a part of the zone, with laser energy ramping up (along the radius) to a maximum allowed energy and staying at that energy. The ramp up region, which is dependent on the predefined OPL difference profile and the (Continued)

maximum allowed energy, is short, and most part of the pass is scanned at the maximum allowed energy.

19 Claims, 3 Drawing Sheets

(58) Field of Classification Search
CPC ...... A61F 2009/0087; A61F 2250/0004; A61F 9/00834; B29D 11/023
See application file for complete search history.

(56) References Cited

U.S. PATENT DOCUMENTS

| 9,192,292 | B2 | 11/2015 | Bille |
| 2011/0212205 | A1 | 9/2011 | Bille |
| 2013/0103144 | A1 | 4/2013 | Bille et al. |
| 2014/0135920 | A1 | 5/2014 | Sahler et al. |
| 2015/0335477 | A1 | 11/2015 | Schuele et al. |
| 2019/0307554 | A1 | 10/2019 | Schuele et al. |

OTHER PUBLICATIONS

International Search Report and Written Opinion for Application No. PCT/IB2020/053419, dated Jun. 25, 2020, 6 pages.

OPTIMIZED WRITING OF REFRACTIVE INDEX STRUCTURES IN IOLS USING VARIABLE PASSES

CROSS-REFERENCES TO RELATED APPLICATIONS

This application is a U.S. national stage of and claims the benefit under 35 U.S.C. § 371 of International Patent Application No. PCT/IB2020/053419, filed Apr. 9, 2020, which claims priority to U.S. Provisional Application Nos. 62/832,825, filed Apr. 11, 2019 and 62/944,328, filed Dec. 5, 2019, all of which are incorporated herein by reference in their entirety.

BACKGROUND OF THE INVENTION

Field of the Invention

This invention relates to post-surgical modification of intraocular lens (IOL), and in particular, it relates to a refractive index modification method for forming a Fresnel-type gradient index lens in the IOL.

Description of Related Art

Despite all the optimization of modern pre-surgical diagnostic and IOL formulas, about 30% of cataract patients are left with visually significant refractive error after cataract surgery. This may include spherical power misses and also misses in matching existing higher order aberrations like chromatic aberrations. These misses—the mismatches between the required optical power and the actual resulting optical power of the IOL—can be corrected post cataract surgery by modifying the lens using a laser.

Post-surgical shape correction of the IOL by UV photo cross linking and the resulting shape change has been demonstrated and commercialized, for example, by RxSight, Inc.

SUMMARY

The present invention is directed to a method of scanning a pulsed laser beam in an IOL to form a Fresnel type gradient index lens.

An object of the present invention is to improve the processing speed of forming a Fresnel type gradient index lens in the IOL.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a method for forming a zone of a Fresnel type gradient index lens in an intraocular lens (IOL), the zone having a ring shape and a predefined radial profile of optical pathlength (OPL) difference, the method including: scanning a pulsed laser beam in the IOL in multiple passes, wherein in each pass, the laser beam is scanned in concentric circles of varying radii within all of part of the zone, and wherein in each of all except a smallest one of the multiple passes, within a first radius range of the zone, the energy of the pulsed laser beam for each circle is below a predefined maximum energy and is dependent on the predefined radial profile of the OPL difference, and within a second radius range of the zone which is non-overlapping with the first radius range, the energy of the pulsed laser beam for each circle is the predefined maximum energy, and wherein in the smallest one of the multiple passes, within a first radius range of the zone, the energy of the pulsed laser beam for each circle is below the predefined maximum energy and is dependent on the predefined radial profile of the OPL difference.

In another aspect, the present invention is directed to an ophthalmic surgical laser system for forming a zone of a Fresnel type gradient index lens in an intraocular lens (IOL), the zone having a ring shape and a predefined radial profile of optical pathlength (OPL) difference, the system including: a laser light source configured to generate a pulsed laser beam; an optical delivery system configured to deliver the pulsed laser beam to the IOL, including a scanner system configured to scan the pulsed laser beam within the IOL; and a controller configured to control the laser light source and the scanner system to perform the above described method.

It is to be understood that both the foregoing general description and the following detailed description are exemplary and explanatory and are intended to provide further explanation of the invention as claimed.

DETAILED DESCRIPTION OF PREFERRED EMBODIMENTS

Commonly owned, co-pending U.S. patent application Ser. No. 16/375,784, filed Apr. 4, 2019, entitled Methods and Systems for Changing a Refractive Property of an Implantable Intraocular Lens ("the '784 application"), describes a "method of altering a refractive property of a crosslinked acrylic polymer material by irradiating the material with a high energy pulsed laser beam to change its refractive index. The method is used to alter the refractive property, and hence the optical power, of an implantable intraocular lens after implantation in the patient's eye. In some examples, the wavelength of the laser beam is in the far red and near IR range and the light is absorbed by the crosslinked acrylic polymer via two-photon absorption at high laser pulse energy . . . . The method can be used to form a Fresnel lens in the optical zone [of the IOL]." (Abstract.) As described in the '784 application, the IOL may be formed of a crosslinked acrylic polymer, and the refractive index modification is achieved through heating of the material. The laser beam may be in the blue range, or the red and near infrared range, in which case the IOL material absorbs the laser light through two-photon absorption. The content of the '784 application is incorporated herein by reference in its entirety.

Figure 3:
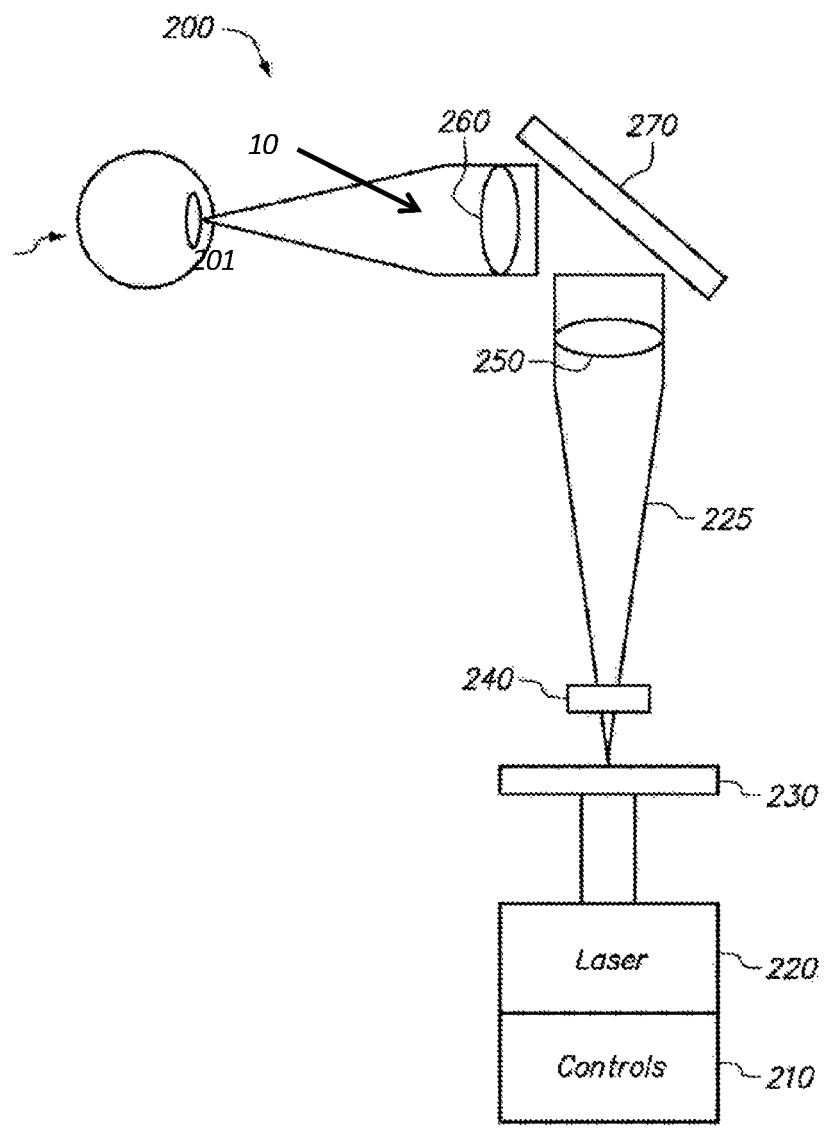
FIG. 3 schematically illustrates an ophthalmic surgical laser system in which embodiments of the present invention can be implemented.

FIG. 3 schematically illustrates an ophthalmic surgical laser system 200 in which embodiments of the present invention can be implemented. The system 200, which can project or scans an optical beam into a patient's eye 201 containing the IOL 10, includes control electronics 210, a laser light source 220, an attenuator 230, a beam expander 240, focusing lenses 250, 260 and reflectors 270. Control electronics 210 may be a computer, microcontroller, etc. with memories storing computer-readable program code to control the operation of various components of the laser system to accomplish the scanning methods described herein. Scanning may be achieved by using one or more moveable optical elements (e.g. lenses 250, 260, reflectors 270) which also may be controlled by control electronics 210, via input and output devices (not shown). Another means of scanning might be enabled by an electro optical deflector device (single axis or dual axis) in the optical path. Although FIG. 3 shows the optical beam directed to a patient's eye, it should be understood that the intraocular lens may be irradiated before placement into the patient's eye in order to customize a refractive property of the intraocular lens.

During operation, the light source 220 generates an optical beam 225 whereby reflectors 270 may be tilted to deviate the optical beam 225 and direct beam 225 towards the patient's eye 201 and particularly into the IOL in order to alter the refractive index of the IOL material. Focusing lenses 250, 260 can be used to focus the optical beam 225 into the patient's eye 201 and the IOL. The positioning and character of optical beam 225 and/or the scan pattern it forms on the eye 201 may be further controlled by use of an input device such as a joystick, or any other appropriate user input device.

Although not shown in FIG. 3, the laser system 200 preferably also includes imaging and visualization sub-systems, such as and without limitation, an optical coherence tomography (OCT) system, a video monitoring system, etc. These sub-systems are used to provide images of and to locate the various anatomical structures of the eye as well as the IOL, which can assist in performance of the various methods described later in this disclosure. Many types of imaging and visualization sub-systems are known in the art and their detailed descriptions are omitted here.

In many embodiments, the light source is a 320 nm to 800 nm pulsed laser source. In many embodiments, the light source 220 is a 320 nm to 800 nm laser source such as an tunable femtosecond laser system or it may be a Nd:YAG laser source operating at the 2nd harmonic wavelength, 532 nm, or 3rd harmonic wavelength, 355 nm.

In operation, the light of the light source is focused and is scanned in the IOL material in order to effect a change of the refractive index in a volume of the material. The shape and volume of the volume whose refractive index is changed is determined by the change in the refractive property of the intraocular lens that is desired.

In embodiments of the present invention, the IOL material is a crosslinked acrylic polymer, made of an optically clear, hydrophobic, acrylic elastomer. Without being limited by theory, one effect of the laser irradiation of the IOL material is to change the hydrophobicity of the acrylic material. As a result, water is expelled from the area in or around the area that has been irradiated, which causes or may cause a change in the refractive index of the material. Another effect of the laser irradiation is to cause local heating of the crosslinked acrylic polymer irradiated with the laser pulses, which causes or may cause a change in the refractive index of the material. The index change typically is proportional to total energy. In embodiments of the present invention, the wavelength of the laser beam is in the far red and near IR range and the light is absorbed by the IOL material via two-photon absorption at high laser pulse energy.

Figure 1:
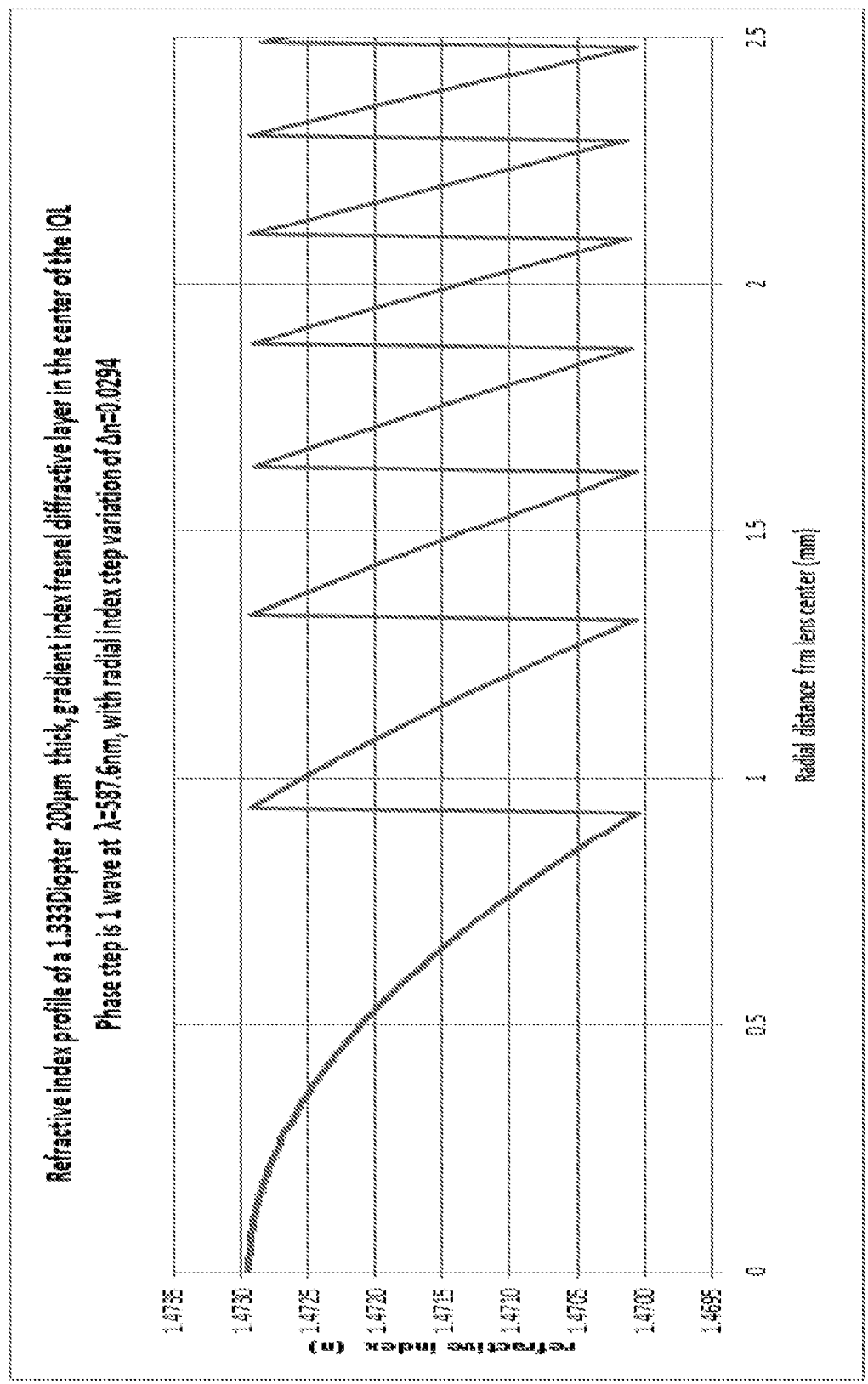
FIG. 1 shows an example of a Fresnel type refractive index profile along a radial direction according to an embodiment of the present invention.

As described in the '784 application, by scanning the laser beam in the IOL in concentric patterns, concentric rings of refractive index variation may be generated, forming a Fresnel type gradient index lens. Such a lens may provide high optical power changes (by adding an optical power to the optical power of the IOL), as high as multiple diopters. FIG. 1 shows an example of a Fresnel refractive index profile along a radial direction from the lens center. The profile has multiple zones, where in each zone, the refractive index n ramps up and then jumps to the unchanged level. To be a Fresnel lens, the size of the jumps (the phase step) between zones should be equivalent to an integer number of waves. The refractive index difference may be expressed by the differences in optical path length (OPL) through the material, where OPL=n*s, s being the thickness of the relevant material (in a more complex case, the OPL is the integral of n over the light propagation path). The Fresnel profile requires the OPL difference to be: $\Delta OPL = \Delta n * s = N\lambda$, where N is an integer and $\lambda$, is the wavelength of the light being refracted.

In the illustrated example, a layer of the IOL material approximately 200 µm thick is modified by the laser with a variable index in a number of annular zones (7 in this case) centered on the optical axis of the IOL. Each zone has a 1 wave difference in OPL from the inner to the outer edge of the zone (which has a parabolic profile in this example), and a 1 wave step transitioning to the next zone. For example, a 7-zone gradient index, Fresnel diffractive lens with a diameter of about 5 mm, has an optical power of 1.333 Diopters.

In practice, it may be difficult to achieve a refractive index change equivalent to a full wave of optical pathlength difference in the IOL by a single pulse of the laser beam. The use of femtosecond laser is a highly energy dependent process to achieve the index change within the material as it is based on multiphoton (e.g., two-photon) absorption. Due to the multiphoton absorption requirement, it is preferred that the system be used at the highest possible energy because the laser photons are more efficiently absorbed at higher energy levels than at lower energy levels. On the other hand, the upper end of useful energy is limited by the change of the process from an induced index change to an induced damage of the IOL material. For these reasons, the required refractive index change at a given location are typically not achieved in a single pass of the laser; rather, the intended pattern of refractive index change is achieved by repeated multiple (e.g., tens to hundreds) laser irradiations. In one method, the irradiation is repeated multiple consecutive times using the same patterns. For example, the laser beam is scanned along a circle at a particular radius for multiple times until the desired OPL difference is achieved.

Figure 2:
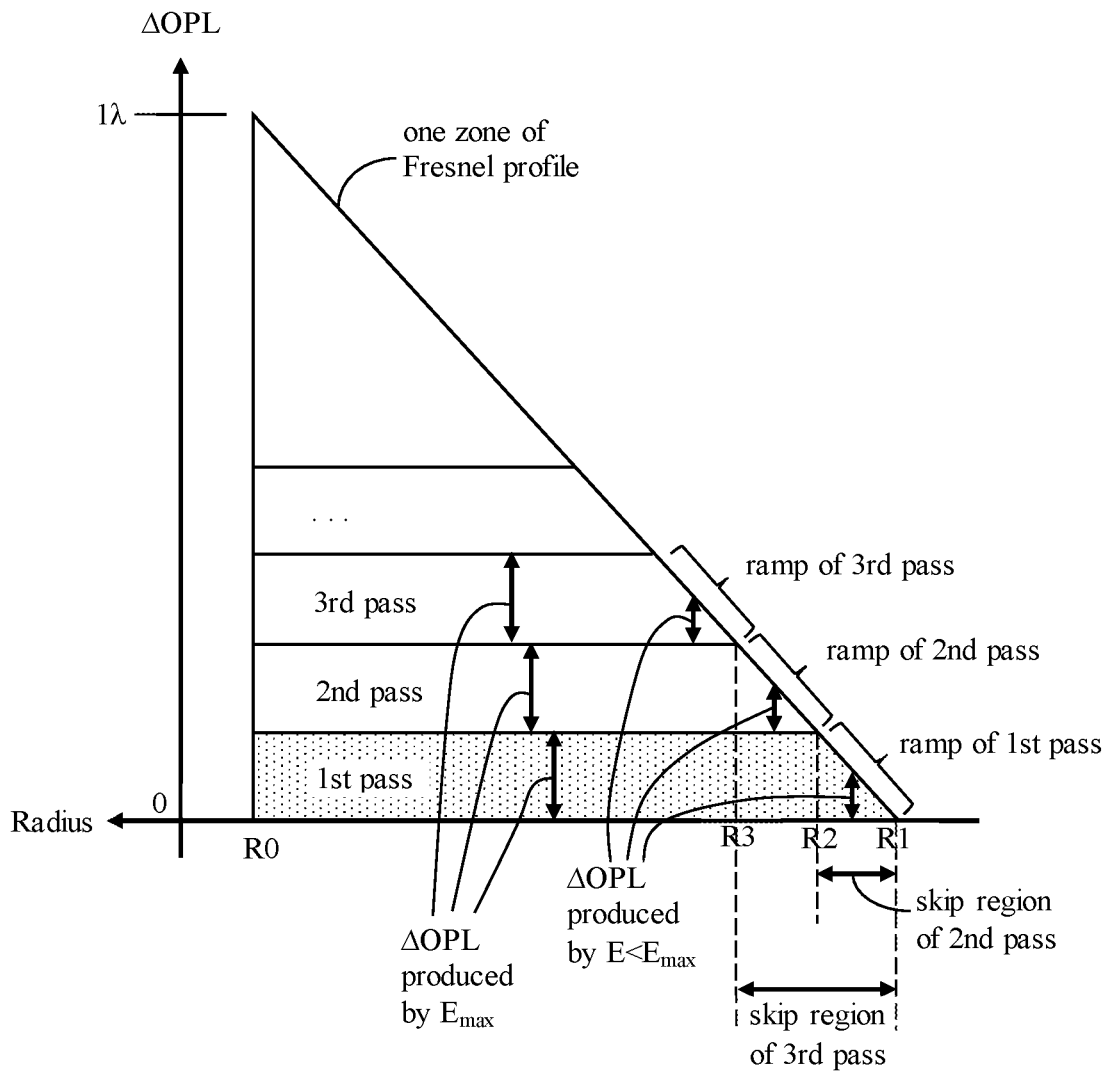
FIG. 2 schematically illustrates a laser beam scanning method for forming a gradient index lens in the IOL.

Embodiments of the present invention uses a different scanning method, as illustrated in FIG. 2. It does not scan the beam in the same pattern multiple consecutive times to add up to the desired OPL difference. Rather, as shown in FIG. 2, to form a zone of a predefined OPL difference profile located between radii R1 and R0 (a zone is a ring shape in the plan view), the laser beam is scanned in multiple passes; in each pass, the laser beam is scanned in concentric circles of varying radii covering all or a part of the zone, with laser energy staying at a maximum energy $E_{max}$ for most of the circles. The maximum energy is the highest allowed laser energy that can be applied to the IOL materials without causing damage to the IOL and/or the eye.

More specifically, as shown in FIG. 2, in the first pass, the scanned circles cover the entire zone from R1 (one boundary of the zone with minimum or zero required OPL difference) to R0 (another boundary of the zone with maximum required OPL difference). Within the radius range from R1 to R2 (referred to as the ramp region), where the required OPL difference as determined by the predefined profile is below what can be achieved by one pass of laser irradiation at the maximum energy, the laser energy for each circle is set at a value that achieves the required OPL difference for that radius. Within the radius range from R2 to R0 (referred to as the maximum energy region), where the required OPL difference is above what can be achieved by one pass of laser irradiation at the maximum energy, the laser energy is set at the maximum energy. In other words, in this pass, the applied laser energy as a function of radius only makes one short ramp to the maximum energy and then stays constant at the maximum energy until the phase step boundary R0 is reached. The location of R2 (the dividing radius between the ramp region and the maximum energy region) is determined by the profile shape of the zone and the OPL difference produced by the maximum energy. Note the scan can alternatively proceed from R0 to R1. The shaded trapezoidal shape in FIG. 2 represents the OPL change achieved by the first pass.

The next (second) pass skips (i.e., does not scan) the region where the first pass applied the energy ramp (i.e., between R1 and R2), and starts ramping just where the ramp of the previous (first) pass stopped (i.e. at R2). For the second pass, within the radius range from R2 to R3, where the remaining required OPL difference—i.e., the OPL difference required by the predetermined profile minus the OPL difference that has been achieved by the previous passes (the first pass)—is below what can be achieved by one pass of laser irradiation at the maximum energy, the laser energy for each circle is set at a value that achieves the remaining required OPL difference for that radius. Within the radius range from R3 to R0, where the remaining required OPL difference is above what can be achieved by one pass of laser irradiation at the maximum energy, the laser energy is set at the maximum energy. Thus, again, a short ramp to the maximum energy is applied and then the energy stays constant at the maximum energy until the phase step boundary R0 is reached. The scan can alternatively proceed from R0 to R2.

Additional passes are performed in a similar manner, consecutively, until the desired full step height of OPL difference is reached at radius R0.

To summarize, the parameters of the multiple passes within a zone may be defined as follows. The zone is a ring shaped area between two phase step boundaries at radius R0 and radius R1. An OPL difference profile desired to be achieved, $\Delta OPL$, is a function of radius defined in the zone, where $\Delta OPL$ is zero at R1 and is a predefined maximum value $\Delta OPLmax$ at R0, and varies monotonously in between. A number of additional radii R2, R3, ... Rm are defined consecutively between R1 and R0, where each Ri (i=2, 3, ..., m) is the radius at which the $\Delta OPL$ profile has a value that is a multiple of $\Delta OPLe$, or more specifically, $\Delta OPLe*(i-1)$, where $\Delta OPLe$ corresponds to the OPL difference produced by one pass of the laser scan at the maximum energy $E_{max}$.

The multiple scan passes are performed between R0 and the respective radii R1, R2, ..., Rm, e.g., the i-th pass is performed between R0 and Ri (i=1, 2, 3, ..., m). In each pass, the laser beam is scanned in concentric circles of varying radii from R0 to Ri (or from Ri to R0). Each pass except for the smallest pass, e.g., the i-th pass (i=1, 2, 3, ..., m−1), has two regions: a ramp region defined as the radius range from Ri to Ri+1, and a maximum energy region defined as the radius range from Ri+1 to R0. The smallest pass, between R0 and Rm, has only a ramp region and no maximum energy region. Within the ramp region of each pass, the laser energy for each circle is set at a value that produces an OPL difference of ($\Delta OPLr$ mod $\Delta OPLe$), or more specifically, ($\Delta OPLr-\Delta OPLe*(i-1)$), where $\Delta OPLr$ is the value of the $\Delta OPL$ profile at the radius r of that circle, and mod is the modulo operation. Within the maximum energy region of each pass, the laser energy is set at the maximum energy $E_{max}$. For each pass except for the largest pass (R1 to R0), the region of the zone between R1 and Ri is a skip region where no laser beam is applied.

From the above descriptions, it can be seen that the ramp regions of all of the passes are non-overlapping with each other and collectively cover the entire zone from R1 to R0, and that the second radius ranges of all except the smallest pass partially overlap each other.

Using this scanning method, radial laser passes have the laser set at the maximum laser energy for much of each pass, which enables highly efficient laser processing at the most efficient energy set point.

In the example shown in FIG. 2, the predefined OPL difference profile of the zone is shown as being approximately linear. However, the method is applicable to all possible shapes of OPL difference profiles required to be achieved so long the profile is monotonic in the zone. For example, the profile of the zone may be parabolic as shown in the example of FIG. 1, or a free form profile, etc. The boundary locations (e.g. R2, R3, etc.) between the ramp region and the maximum energy region for each pass is determined by the profile shape and the OPL difference produced by the maximum laser energy.

In some embodiments, for scanned circles belonging to different passes that are located at the same radius, the laser focus positions may be shift slightly in the circumferential direction (e.g., angular direction) so they do not overlap, to avoid overdelivering laser energy in one focal area. This is advantageous particularly in areas that require a high number of passes. It allows a more uniform distribution within the IOL material and avoids possible damage due to multiple laser focus spots overlapping.

The depth of each scan pattern may also be adjusted to correct a focus depth shift effect due to multiphoton absorption. In multiphoton absorption, due to the high beam energy, the location where absorption occurs may shift away from the intended focus spot of the laser beam and toward the incident beam. This is caused by the energy of the laser pulse being absorbed and even depleted shortly before it reaches the intended focus spot due to the onset of two-photon absorption in the volume in front of the focus, as the power density becomes sufficiently high in that volume due to focusing and exceeds the threshold of two-photon absorption. Thus, in the above described scanning method, the depth location of beam absorption may be different when the applied laser energy is different. In some embodiments of the present invention, to compensate for such differences in the beam absorption locations, the intended focus position of the beam may be dynamically adjusted accordingly, to ensure that the planned effect depth is achieved for all beam energies.

In some embodiments, the variation of laser energy of the scans in the ramp regions is accomplished by varying the energy per pulse of the laser beam. In an alternative embodiment, the variation of laser energy in the ramp regions may be achieved by utilizing variable laser spot spacing of the scanned circles, either alone or in combination with varying the pulse energy of the incident laser pulses. Larger lateral spacing (lower spot density) will lead to lower refractive index change per unit area, while higher spot density will lead to higher refractive index change per unit area.

In some alternative embodiments, the various passes may be carried out in other orders. For example, referring again to FIG. 2, if the passes are designated 1st, 2nd, 3rd, . . . nth which cover successively narrower rings of the profile zone (i.e., with successively larger skip regions), the passes may be performed in the order of 1st, nth, 2nd, (n−1)th, 3rd, (n−2)th, . . . . This orders allows for additional effective space in between the different passes. Other orders are also possible.

Although the scan pattern are described above as being circles, they may alternatively be ellipses or arcs (i.e. parts of full circles), and the ring shaped zone may correspondingly be elliptical shaped or be an angular segment of a circular ring.

In the above-described scanning method, the multiple scanning passes may be performed at the same depth of the IOL material, or at slightly different depths. Because the OPL of a given light propagation path is the integral of the refractive index over the distance, the total OPL difference at each radius is the same regardless of whether the multiple scanning passes occur at the same depth or slightly different depths. Thus, in some embodiments, a spatial depth separation may be introduced to the different passes. In preferred embodiments, the different passes are performed at substantially the same depth, except for possible focus depth shift effect due to multiphoton absorption.

Using the scanning method according to various embodiments of the present invention, much higher processing efficiency can be achieved which make the application more practicable in a patient's eye. The method highly increases the processing speed and makes the application usable in a treatment environment.

It will be apparent to those skilled in the art that various modification and variations can be made in the method and related apparatus of the present invention without departing from the spirit or scope of the invention. Thus, it is intended that the present invention cover modifications and variations that come within the scope of the appended claims and their equivalents.

What is claimed is:

1. A method for forming a zone of a Fresnel type gradient index lens in an intraocular lens (IOL), the zone having a ring shape and a predefined radial profile of optical pathlength (OPL) difference, the method comprising:
   scanning a pulsed laser beam in the IOL in multiple consecutive passes,
   wherein in each pass, the laser beam is scanned in concentric circles of varying radii within all of part of the zone,
   wherein in each of all except a smallest one of the multiple passes, within a first radius range of the zone, an energy of the pulsed laser beam for each circle is below a predefined maximum energy and is dependent on the predefined radial profile of the OPL difference, and within a second radius range of the zone which is non-overlapping with the first radius range, the energy of the pulsed laser beam for each circle is the predefined maximum energy, and
   wherein in the smallest one of the multiple passes, within a first radius range of the zone, the energy of the pulsed laser beam for each circle is below the predefined maximum energy and is dependent on the predefined radial profile of the OPL difference.

2. The method of claim 1, wherein the predefined radial profile of OPL difference is monotonous with radius.

3. The method of claim 1, wherein the first radius ranges of all of the multiple passes are non-overlapping with each other and collectively cover an entirety of the zone.

4. The method of claim 1, wherein the second radius ranges of all except a smallest one of the multiple passes partially overlap each other.

5. The method of claim 1, wherein the maximum energy is a highest laser energy of the pulsed laser beam that avoids causing damage to the IOL when applied to the IOL.

6. The method of claim 1, wherein within the first radius range for each pass, the energy of the pulsed laser beam for each circle is $\Delta OPLr$ mod $\Delta OPLe$, where $\Delta OPLr$ is a value of the predefined radial profile of the OPL difference at a radius of the circle, and $\Delta OPLe$ is an OPL difference produced by one pass of the pulsed laser beam at the maximum energy, and mod is a modulo operation.

7. The method of claim 1, wherein a first scanned circle of a first one of the multiple passes and a second scanned circle of a second one of the multiple passes have the same radius, and wherein laser pulses of the first scanned circle and laser pulses of the second scanned circle are shifted relative to each other in a circumferential direction and are free of overlapping.

8. The method of claim 1, wherein in the first radius range of each pass, the energy of the pulsed laser beam is varied between different circles by varying an energy per pulse of the pulsed laser beam and/or by varying a spacing of the laser pulses in the IOL.

9. The method of claim 1, wherein the multiple passes are performed at a same depth of the IOL.

10. The method of claim 1, wherein the IOL material is a crosslinked acrylic polymer made of an optically clear, hydrophobic, or acrylic elastomer.

11. An ophthalmic surgical laser system for forming a zone of a Fresnel type gradient index lens in an intraocular lens (IOL), the zone having a ring shape and a predefined radial profile of optical pathlength (OPL) difference, the system comprising:
   a laser light source configured to generate a pulsed laser beam;
   an optical delivery system configured to deliver the pulsed laser beam to the IOL, including a scanner system configured to scan the pulsed laser beam within the IOL; and
   a controller configured to control the laser light source and the scanner system to scan scanning a pulsed laser beam in the IOL in multiple consecutive passes,
   wherein in each pass, the laser beam is scanned in concentric circles of varying radii within all of part of the zone,
   wherein in each of all except a smallest one of the multiple passes, within a first radius range of the zone, an energy of the pulsed laser beam for each circle is below a predefined maximum energy and is dependent on the predefined radial profile of the OPL difference, and within a second radius range of the zone which is non-overlapping with the first radius range, the energy of the pulsed laser beam for each circle is the predefined maximum energy, and
   wherein in the smallest one of the multiple passes, within a first radius range of the zone, the energy of the pulsed laser beam for each circle is below the predefined maximum energy and is dependent on the predefined radial profile of the OPL difference.

12. The system of claim 11, wherein the predefined radial profile of OPL difference is monotonous with radius.

13. The system of claim 11, wherein the first radius ranges of all of the multiple passes are non-overlapping with each other and collectively cover an entirety of the zone.

14. The system of claim 11, wherein the second radius ranges of all except a smallest one of the multiple passes partially overlap each other.

15. The system of claim 11, wherein the maximum energy is a highest laser energy of the pulsed laser beam that avoids causing damage to the IOL when applied to the IOL.

16. The system of claim 11, wherein within the first radius range for each pass, the energy of the pulsed laser beam for each circle is $\Delta OPLr \bmod \Delta OPLe$, where $\Delta OPLr$ is a value of the predefined radial profile of the OPL difference at a radius of the circle, and $\Delta OPLe$ is an OPL difference produced by one pass of the pulsed laser beam at the maximum energy, and mod is a modulo operation.

17. The system of claim 11, wherein a first scanned circle of a first one of the multiple passes and a second scanned circle of a second one of the multiple passes have the same radius, and wherein laser pulses of the first scanned circle and laser pulses of the second scanned circle are shifted relative to each other in a circumferential direction and are free of overlapping.

18. The system of claim 11, wherein in the first radius range of each pass, the energy of the pulsed laser beam is varied between different circles by varying an energy per pulse of the pulsed laser beam and/or by varying a spacing of the laser pulses in the IOL.

19. The system of claim 11, wherein the multiple passes are performed at a same depth of the IOL.

* * * * *